United States Patent
Miyakawa et al.

(10) Patent No.: US 7,154,597 B2
(45) Date of Patent: Dec. 26, 2006

(54) METHOD FOR INSPECTING SURFACE AND APPARATUS FOR INSPECTING IT

(75) Inventors: Kazuhiro Miyakawa, Tokyo (JP); Yoichiro Iwa, Tokyo (JP); Akihiko Sekine, Tokyo (JP)

(73) Assignee: Kabushiki Kaisha Topcon, Tokyo (JP)

(*) Notice: Subject to any disclaimer, the term of this patent is extended or adjusted under 35 U.S.C. 154(b) by 319 days.

(21) Appl. No.: 10/879,856

(22) Filed: Jun. 29, 2004

(65) Prior Publication Data
US 2004/0263835 A1  Dec. 30, 2004

(30) Foreign Application Priority Data
Jun. 30, 2003 (JP) ............. 2003-188102

(51) Int. Cl.
G01N 21/00 (2006.01)
(52) U.S. Cl. ................. 356/237.2; 356/237.4
(58) Field of Classification Search ............. None
See application file for complete search history.

(56) References Cited

U.S. PATENT DOCUMENTS 5,098,191 A * 3/1992 Noguchi et al. ............ 356/394
6,204,918 B1  3/2001 Isozaki et al.
6,727,987 B1 * 4/2004 Yonezawa ............... 356/237.2

FOREIGN PATENT DOCUMENTS

JP   56-067739   6/1981
JP   11-295229   10/1999

OTHER PUBLICATIONS

U.S. Appl. No. 10/864,062, filed Jun. 9, 2004, Miyakawa et al.

* cited by examiner

Primary Examiner—Michael P. Stafira
(74) Attorney, Agent, or Firm—Chapman and Cutler LLP

(57) ABSTRACT

A method for inspecting a surface, including entering a predetermined luminous flux at a predetermined incident angle in an inspected surface of an inspection object which is an object of a surface inspection, displaying relatively at least one of the luminous flux and the inspection object so that the luminous flux scans upon the inspected surface, decomposing spatially light intensity of scattered light reflected on an area of the inspected surface entering the luminous flux into a plurality of channels with respect to an one-dimensional direction corresponding to a predetermined direction in the area of the inspected surface entering the light flux, performing inspection of the inspected surface by detecting individually light intensity of each of the decomposed scattered lights obtained by the decomposition, and increasing uniformity of light intensity distribution with respect to at least the predetermined direction in the area of the inspected surface in which the luminous flux is entered.

9 Claims, 9 Drawing Sheets

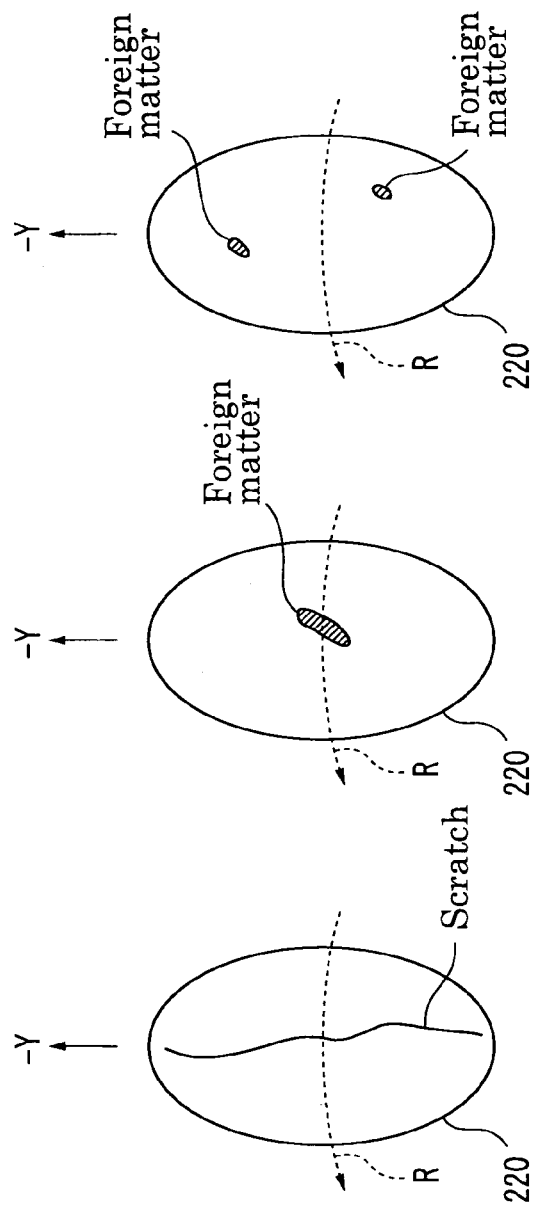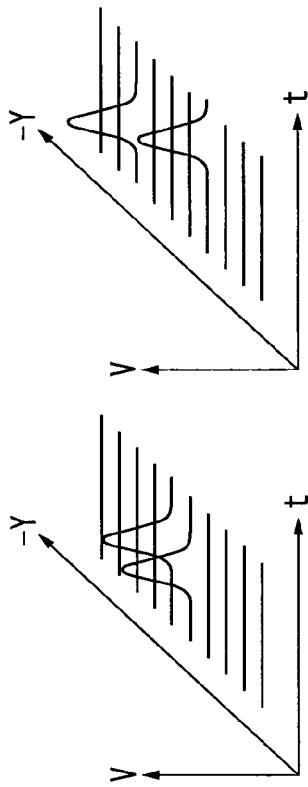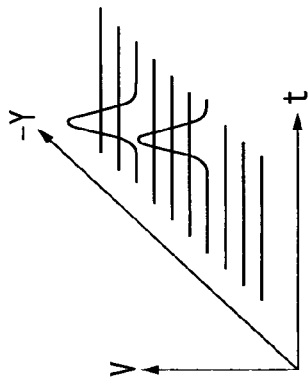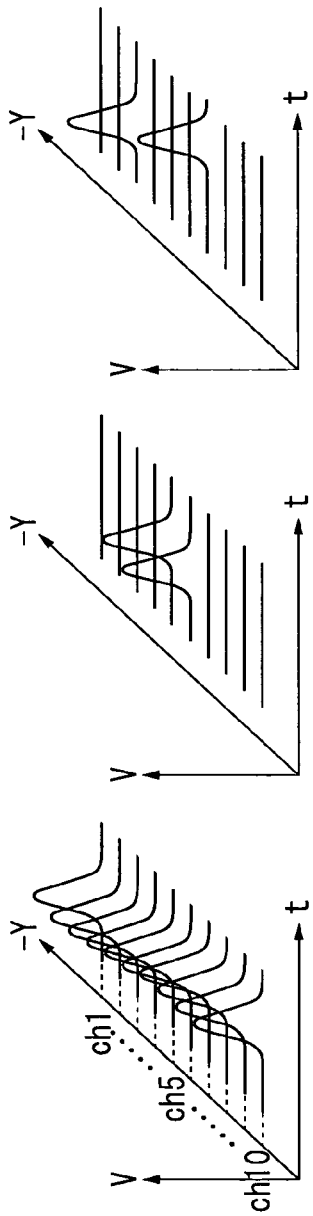

METHOD FOR INSPECTING SURFACE AND APPARATUS FOR INSPECTING IT

CROSS-REFERENCE TO RELATED APPLICATION

The application claims the priority benefit of Japanese Patent Application No. 2003-188102, filed on Jun. 30, 2003.

FIELD OF THE INVENTION

The present invention relates to a method and an apparatus for inspecting a surface, more particularly to an improvement in a method and an apparatus for inspecting a defect on a surface to be inspected or inspected surface by irradiating a luminous flux on the inspected surface and detecting intensity of scattered light reflected on the inspected surface.

RELATED ART STATMENT

Conventionally, there has been known a surface inspection apparatus for detecting a defect on a surface to be inspected of an inspection object such as a semiconductor wafer, for example, the defect being such as a foreign matter attached to the inspected surface or one or more scratches (including a crystal defect) generated on the inspected surface.

The surface inspection apparatus, for example, comprises a light source for emitting a predetermined luminous flux such as a laser beam, an optical system for irradiating the luminous flux emitted from the light source on the inspected surface at a predetermined irradiation angle, a scanning device for displacing the inspection object in such a manner that the luminous flux scans the inspected surface, a light intensity detecting device for detecting intensity of the irradiated luminous flux, and a scattered light detecting optical system for guiding scattered light emitted from an area or irradiation area in which the luminous flux is irradiated, to the light intensity detecting device.

The surface inspection apparatus inspects presence and absence of the defect depending upon the intensity of the scattered light inspected by the light intensity detecting device (see JP-A-S56-67739).

Here, the scattered light from the irradiation area means light scattering in a direction other than the direction in which the luminous flux irradiated on the inspected surface regularly reflects in the irradiation area.

Therefore, an optical axis of the scattered light detecting optical system is set in the direction other than the regular reflection direction, and the optical axis is set to direct to the irradiation area at a predetermined depression angle with respect to the inspected surface, for example.

Moreover, the Applicant has proposed a method and an apparatus for inspecting a surface in which the scattered light is decomposed into a plurality of channels with respect to at least a one-dimensional direction and these decomposed scattered lights are detected, to enable to discriminate singular or plural numbers, a size, a classification or the like of the defect in the irradiation area (see Japanese Patent Application 2003-165458).

However, if the scattered light is decomposed into the plurality of channels and detected, although it is possible to detect the size and so on of the aforementioned defect only depending on whether the scattered light is detected every each channel, if analysis of the defect is performed based on high and low of the intensity of the scattered light detected every each channel, it is necessary to detect accurately magnification of the intensity of the scattered light.

On the other hand, the luminous flux entered in the inspected surface has no uniformity of light intensity distribution in a transverse section of the inspected surface, when it is a laser beam, for example, and the laser beam has generally Gaussian distribution. In this way, when the luminous flux, which the light intensity distribution is not uniform, is entered in the inspected surface, the area of the inspected surface in which the luminous flux is entered has spatially and justifiably characteristic of light intensity distribution depending on the light intensity distribution of the entered luminous flux.

In the other words, entered in a portion in which beam center of the laser beam is entered, of the area of the inspected surface in which the laser beam is entered is light having light intensity higher than that in an area in which beam periphery of the laser beam is entered, and therefore, even if the same defect is existed on the area and the portion, respectively, the light intensity detected in the channel corresponding to the portion in which the beam center is entered is higher than that detected in the channel corresponding to the area in which the beam periphery is entered. Consequently, the analysis of the defect or the like cannot be accurately performed based on the magnification of the detected light intensity.

SUMMARY OF THE INVENTION

The present invention has been made in view of the aforementioned problems, and it is, therefore, an object of the present invention to provide a method and an apparatus for inspecting a surface in which when scattered light is decomposed and detected into a plurality of channels, un-uniformity of intensity of detected light depending on un-uniformity of light intensity distribution in an area of an inspected surface in which luminous flux is entered, can be reduced or eliminated.

To attain the above object, according to an aspect of the present invention, there are provided a method and an apparatus for inspecting a surface in which uniformity of the light intensity distribution in the area of the inspected surface can be previously increased with respect to at least a predetermined direction or a direction corresponding to a one-dimensional direction in which the plurality of channels are arranged, before detecting the scattered light, and therefore the un-uniformity of intensity of the detected light can be reduced.

More specifically, the method comprises entering a predetermined luminous flux at a predetermined incident angle in the inspected surface of an inspection object which is an object of a surface inspection, displaying relatively at least one of the luminous flux and the inspection object so that the luminous flux scans upon the inspected surface, decomposing spatially light intensity of the scattered light reflected on the area of the inspected surface entering the luminous flux into a plurality of channels with respect to an one-dimensional direction corresponding to a predetermined direction in the area of the inspected surface entering the light flux, performing inspection of the inspected surface by detecting individually light intensity of each of the decomposed scattered lights obtained by the decomposition, and increasing the uniformity of light intensity distribution with respect to at least the predetermined direction in the area of the inspected surface in which the luminous flux is entered.

Here, the inspection object includes typically semi-conductor wafer or various substrates, but is not limited to them.

The inspection object may include all objects capable of performing inspection of a surface by detecting a foreign matter attached on the inspected surface or presence or absence of scratches generated on the inspected surface and a position of the foreign matter or the scratches.

It is preferable to use laser beam having a high possibility of interference as the luminous flux, which is entered in the inspected surface.

The words, "with respect to at least the one-dimension direction" mean decomposing the scattered light into the plurality of channels not only in one-dimensional direction in an entered plane of light, but also a direction in the entered plane, perpendicular to the one-dimensional direction, namely, in a two-dimensional matrix, and detecting the decomposed scattered lights.

The above will be applied similarly to the following explanation.

The words, "increasing uniformity of light intensity distribution in the area of the inspected surface in which the luminous flux is entered" mean increasing uniformity of distribution of light receiving intensity based on the luminous flux entered in the area of the inspected surface, on which the scattered light is emitted. It is preferable to substantially equalize the distribution of light receiving intensity.

According to the method for inspecting a surface, structured as described above, because the uniformity of light intensity distribution in the area of the inspected surface in which the luminous flux is entered, is increased, the intensity of the detected scattered light depending potentially on the light intensity distribution in the area of the inspected surface is substantially the same value, regardless of a position of the defect existed in the area of the inspected surface.

In other words, only the detected channel is changed according to a position of presence of the defect, namely there is spatial dependency of the detected channel, without the intensity of the decomposed scattered light detected by the presence of the defect being a in a different value according to the position of presence of the defect in the area of the inspected surface, namely there is no spatial dependency of the intensity value.

Of course, the intensity value itself is different according to a concave and convex amount of the defect or the like, but this does not depend on the light intensity distribution in the area of the inspected surface whereas depends on gravity of the defect.

Accordingly, it is possible to detect accurately the intensity of the decomposed scattered light every each channel.

In addition, it is possible to perform a detailed analysis of the defect such as the gravity of the defect based on the magnification of the intensity of the decomposed scattered light by detecting accurately the intensity of the decomposed scattered light.

According to another aspect of the present invention, there is provided an apparatus for inspecting a surface, comprising light source for emitting a predetermined luminous flux, an irradiating optical system for entering at a predetermined incident angle the luminous flux emitted from the light source into an inspected surface of an inspection object which is an object of a surface inspection, a scanning device to relatively displace at least one of said luminous flux and said inspection object so that said luminous flux scans on the inspected surface, a light intensity detecting device to detect intensity of the entered light, and a scattered light detecting optical system for guiding scattered light emitted from an area of the inspected surface in which the luminous flux is entered into the light intensity detecting device.

The light intensity detecting device is set to decompose the scattered light into a plurality of channels at least in a one-dimensional direction in an inclined plane of the light intensity detecting device and to detect the light intensity, in order to increase uniformity of light intensity distribution with respect to at least the predetermined direction in the area of the inspected surface in which the luminous flux is entered.

Here, the inspection object includes typically semi-conductor wafer or various substrates, but is not limited to them. The inspection object may include all objects capable of performing inspection of a surface by detecting a foreign matter attached on the inspected surface or presence or absence of scratches generated on the inspected surface and a position of the foreign matter or the scratches.

It is preferable to use a laser source, for example, a semi conductor laser source LD, an argon ion laser source and so on which emit laser light having a high possibility of interference, as the luminous flux, which is entered in the inspected surface.

A direction of an optical axis of the optical system for detecting the scattered light may be set in such a manner that at least one portion of the scattered light other than regularly reflected light emitted from the area or irradiation area of the inspected surface can be collected, for example, in such a manner that scattered light in a direction perpendicular substantially to a traveling direction of entered luminous flux when the luminous flux is projected on the inspected surface, is collected.

Because the one-dimensional direction in an entered plane of the light intensity detecting device corresponds to the predetermined direction in the area of the inspected surface, in which the luminous flux is entered, when the scattered light is decomposed into the plurality of channels with respect to the one-dimensional direction, each decomposed scattered light is emitted from each separated portion in which the irradiation areas is separated with respect to predetermined directions.

Consequently, because the intensity of the scattered light can be detected every a position or position corresponding to the predetermined direction, in the irradiation area in which the luminous flux is entered, by detecting individually the intensity of each decomposed scattered light, it is possible to enhance detecting resolution of the position of the defect in the position or surface that the scattering of light is generated.

The defect is adapted to discriminate either a plurality of scattered small defects or continued large defects by comparing sequentially intensity of each detected light of the plurality of channels arranged in the one-dimensional direction between adjacent channels.

Meanwhile, the light intensity detecting device configured to decompose and detect the entered scattered light into the plurality of channels with respect to the one-dimensional direction in the entered plane may use typically, for example, a multi-anode photoelectron multiplier or PMT, photo-multiplier or the like, but is not limited to the multi-anode PMT, and may be a configuration in which a plurality of multi-channel type light receivers and a plurality of single-channel light receivers are arranged corresponding to each of the channels.

The words, "with respect to at least the one-dimension direction" mean decomposing the scattered light into the plurality of channels not only in one-dimensional direction in an entered plane of light, but also a direction in the entered plane, perpendicular to the one-dimensional direction, namely, in a two-dimensional matrix, and detecting the decomposed scattered lights.

The words, "increasing uniformity of light intensity distribution in the area of the inspected surface in which the luminous flux is entered" mean increasing uniformity of distribution of light receiving intensity based on the luminous flux entered in the area of the inspected surface, on which the scattered light is emitted. It is preferable to substantially equalize the distribution of light receiving intensity.

According to the apparatus for inspecting a surface, structured as described above, because the uniformity of light intensity distribution in the area of the inspected surface in which the luminous flux is entered, is increased, the intensity of the detected scattered light depending potentially on the light intensity distribution in the area of the inspected surface is substantially the same value, regardless of a position of the defect existed in the area of the inspected surface.

In other words, only the detected channel is changed according to a position of presence of the defect, namely there is spatial dependency of the detected channel, without the intensity of the decomposed scattered light detected by the presence of the defect being a in a different value according to the position of presence of the defect in the area of the inspected surface, namely there is no spatial dependency of the intensity value.

Accordingly, it is possible to detect accurately the intensity of the decomposed scattered light every each channel.

In addition, it is possible to perform a detailed analysis of the defect such as the gravity of the defect based on the magnification of the intensity of the decomposed scattered light by detecting accurately the intensity of the decomposed scattered light.

According to another aspect of the present invention, there is provided a method for inspecting a surface comprising entering a predetermined luminous flux at a predetermined incident angle in an inspected surface of an inspection object, which is an object of a surface inspection, displaying relatively at least one of the luminous flux and the inspection object so that the luminous flux scans upon the inspected surface, decomposing spatially light intensity of scattered light reflected on an area of the inspected surface entering the luminous flux into a plurality of channels in an one-dimensional direction corresponding to a predetermined direction in the area of the inspected surface entering the luminous flux, performing inspection of the inspected surface by detecting individually light intensity of each of the decomposed scattered lights obtained by the decomposition, and standardizing light intensity distribution of the detected decomposed scattered lights in the one-dimensional direction, according to the light intensity distribution with respect to at least the predetermined direction in the area of the inspected surface in which the luminous flux is entered.

Here, the words, "standardizing light intensity distribution of the detected decomposed scattered lights in the one-dimensional direction, according to the light intensity distribution with respect to at least the predetermined direction in the area of the inspected surface" mean performing treatment of compensation in such a manner that un-uniformity of intensity of received light is deemed to be virtually uniform, according to distribution of the intensity of received light due to the entered luminous flux with respect to at least the predetermined direction in the area of the inspected surface.

In other words, if the light intensity distribution in the area of the inspected surface is un-uniform, the light intensity of the decomposed scattered light detected under the above un-uniformity is compensated to the light intensity of the decomposed scattered light which will be detected if the light intensity distribution in the area of the inspected surface is uniform, by signal processing or after-treatment of gain or the like.

Here, the compensating rate and the gain or the like to standardize may be obtained previously experimentally every the decomposed scattered light from the area of the inspected surface by use of a standard inspection object.

According to the method structured in this way, it is possible to obtain an accurate light intensity of the decomposed scattered light by standardizing the light intensity of the detected decomposed scattered light without depending on un-uniformity of the light intensity distribution in the area of the inspected surface.

Moreover, it is possible to accomplish a detailed analysis of the defect such as the gravity of the defect based on the magnification of the intensity of the decomposed scattered light obtained accurately in this way.

Here, there is case that the area of the inspected surface, which is a region of the inspection object, on which the scattered light is reflected, does not coincide accurately with the area of the inspected surface in which the luminous flux is entered.

In other words, although the area of the inspected surface in which the luminous flux is entered is the irradiation area as described above, conventionally, in the irradiation area, because the intensity of the received light has the Gaussian distribution as described above, the intensity of the received light is very low in the vicinity of a peripheral portion of the irradiation area, and therefore the intensity of the scattered light emitted from the vicinity of the peripheral portion is also low. As a result, reliability of analysis based on the scattered light detected in the vanity of the peripheral portion is low.

Consequently, it is preferable to detect only the scattered light from a portion in the vicinity of a center of the luminous flux than the peripheral portion by neglecting the scattered light from a region of the peripheral portion, without a region of detected object of the scattered light being not set to the whole of the irradiation area.

For example, when the intensity or the maximum intensity of the Gaussian distribution of the received light in the center of the luminous flux is I0, if an area of intensity of the received light less than the intensity of $I0/e^2$ is not set as the detected object of the scattered light, an area identical with or more than the intensity of $I0/e^2$, which is the detected object, is deemed newly to be the irradiation area, namely, the area of the inspected surface and is applied as the present invention.

However, even if the area of the received light has intensity less than $I0/e^2$, according to the present invention, a region of the detected object can be enlarged by setting the region in which the intensity is less than a predetermined value to an object increasing the uniformity of the intensity distribution.

On the other hand, if the inspection object which is an object for scanning is a circular plate like shape as the semi conductor wafer, for example and a spiral scan locus which is a combination of a main scan in a rotational direction and a sub scan in a radial scan is adopted, a direction to which the spiral scan locus extends is a direction of scanning and a direction perpendicular to this direction is a direction of pitch in the scanning locus.

Furthermore, it is possible to scan the entire inspected surface even if the pitch of the scanning locus is enlarged if the predetermined direction or a direction of decomposing spatially and detecting the scattered light, in the area of the inspected surface is set to a direction or the direction of pitch, substantially perpendicular to the canning direction, while enlarging the region of detected object in accordance with the present invention, as described above.

BRIEF DESCRIPTION OF THE DRAWINGS

FIGS. 4A, 4B, 4C, 4D, 4E, and 4F are views illustrating a relationship between a type of and a state of a defect in FIGS. 4A, 4B, and 4C and detecting light intensity in FIGS. 4D, 4E, and 4F.

FIG. 7 is a view illustrating a relationship between a magnification of the irradiation area on the inspected surface and a pitch of a scanning locus in which FIG. 7A illustrates a case of the irradiation area similar to that in the prior art and FIG. 7B illustrates a case of an enlarged real irradiation area.

DETAILED DESCRIPTION OF THE PREFERRED EMBODIMENTS

Hereinafter, several embodiments of a method and an apparatus for inspecting a surface according to the present invention will be described with reference to the accompanying drawings.

First Embodiment

Figure 1:
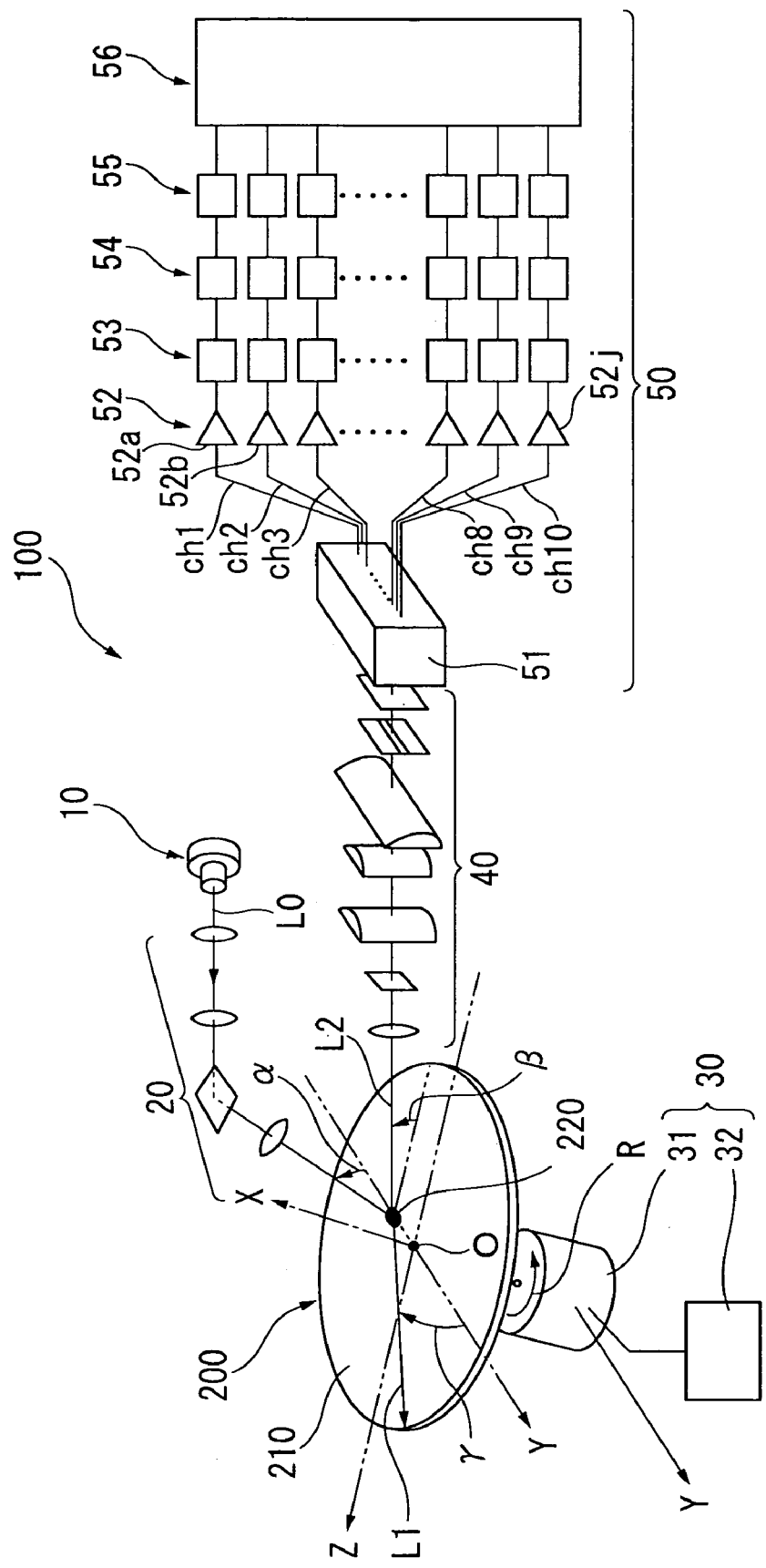
FIG. 1 is a schematic structural view illustrating a surface inspection apparatus according to a first embodiment of the present invention.

FIG. 1 illustrates an apparatus 100 for inspecting a surface in a first embodiment of the present invention.

The surface inspection apparatus 100 comprises a semiconductor laser light source (hereinafter referred to as LD) 10 for emitting a laser beam L0, an irradiation optical system 20 for projecting or entering the laser beam L0 emitted from the LD 10 onto or into an inspected surface 210 of a wafer or inspection object 200 of a substantially real circular plate at a predetermined depression angle $\alpha$ (=incident angle (90°–$\alpha$)), a scanning device 30 for displacing the wafer 200 in such a manner that the laser beam L0 scans the inspected surface 210 in spiral shape (see FIG. 2A), a light intensity detecting device 50 for detecting intensity of the projected or entered light, and a scattered light detecting optical system 40 for guiding a scattered light L2 reflected on a portion (hereinafter referred to as irradiation area) of the inspected surface 210 in which the laser beam L0 is entered, to the light intensity detecting device 50.

Here, the light intensity detecting device 50 is set in such a manner that the scattered light L2 is decomposed or separated into 10 channels (ch) in a one-dimensional direction (Y axial direction) of an incident plane of the entered light in the light intensity detecting device 50, and the decomposed 10 channels are detected, as described later.

If orthogonal axes in the inspected surface 210 of the wafer 200 are set as Y and Z axes, and an axis perpendicular to the inspected surface 210 is set as an X axis, the inspected surface 210 is kept in an inclined state which is slightly turned about the Y axis of a horizontal axis. As a result, the X axis is inclined to a vertical axis with respect to a horizontal plane (see FIGS. 1 and 2B).

Figure 2A:
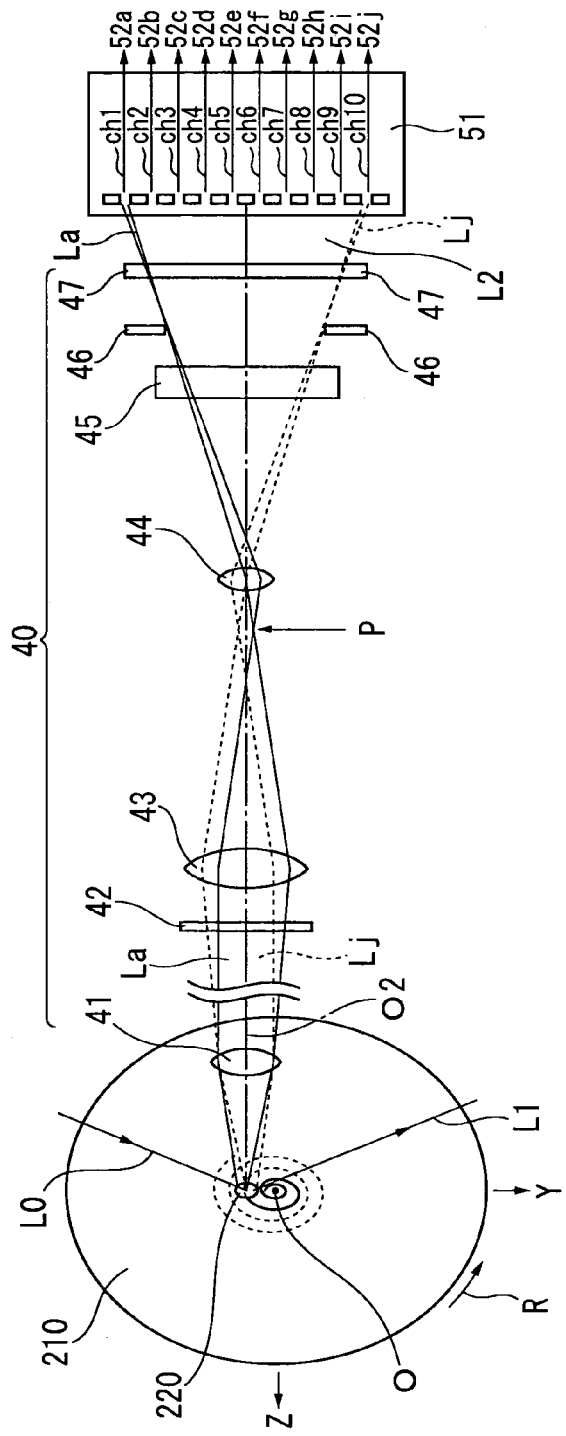
FIG. 2A is a plan view mainly illustrating an optical system for detecting scattered light and a device for detecting light intensity in the surface inspection apparatus shown in FIG. 1.
Figure 2B:
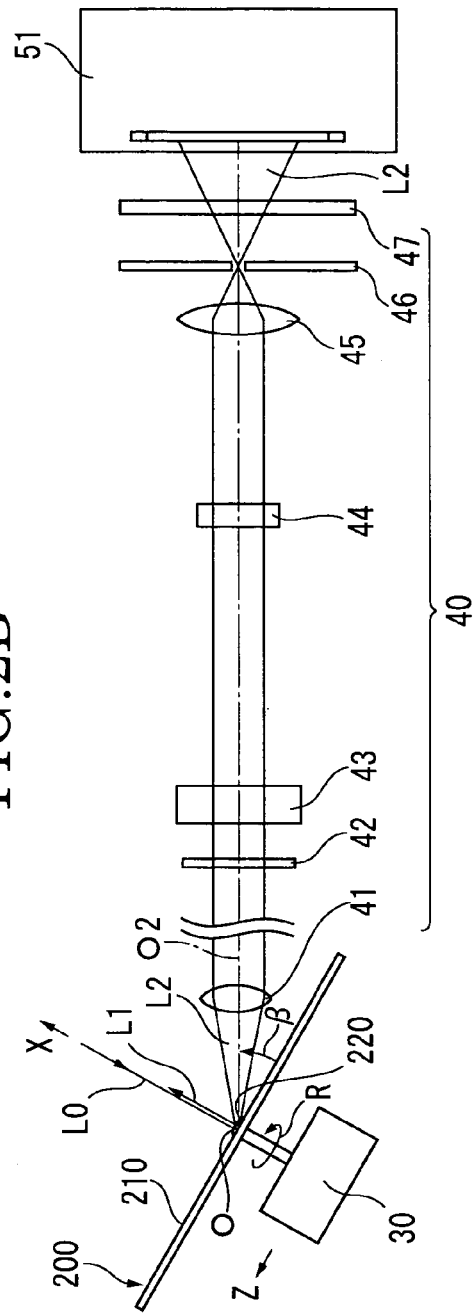
FIG. 2B is a side view illustrating the same scattered light detecting optical system and light intensity detecting device.

The laser beam L0 emitted from the LD10 is guided in XY surfaces to the irradiation area 220 by the irradiation optical system 20. Accordingly, if the laser beam L0 is projected on the inspected surface 210 along the X axis, a projection locus thereof overlaps with the Y axis. Meanwhile, in a plan view as shown in FIG. 2A, the projection locus becomes a locus along the vertical axis of the horizontal plane, so that the projection locus of the laser beam L0 onto the inspected surface 210 does not overlap with the Y axis.

Reflection light L1 of the laser beam L0 which is regularly reflected on the irradiation area 220 is emitted from the irradiation area 220 at an elevation angle $\gamma$ (reflection angle (90°–$\alpha$)).

The irradiation area 220 which is a laser spot formed on the inspected surface 210 by the incidence of the laser beam L0 onto the inspected surface 210 has a substantially elliptical shape having a major axis in the Y axial direction.

The scanning device 30 comprises a turning stage or turning device 31 for turning the wafer 200 about a center O thereof as a turning center or the X axis and a liner motor or liner movement device 32 for linearly moving the wafer 200 together with the turning stage 31 in the Y axial direction.

The laser beam L0 scans the wafer 200 in a spiral state, while turning the wafer 200 by the turning stage 31 and linearly displacing the wafer 200 by the liner motor 32.

An optical axis O2 of the scattered light detecting optical system 40 is substantially perpendicular to the Y axis, is directed to the irradiation area 220, and is disposed at a depression angle $\beta$ (in this embodiment $\beta$=30°) with respect to the inspected surface 210. The scattered light detecting optical system 40 converges or collects scattered light L2 scattering in a direction other than reflection light L1 reflected on the irradiation area 220, and guides the converged scattered light L2 to the light intensity detecting device 50.

Here, the scattered light detecting optical system 40 comprises, in order of an upstream side in an advancing direction of the scattered light L2, a condenser lens 41 for converging the scattered light L2 emitted from the irradiation area 220, a polarizing plate 42 for adjusting a wave surface of the entered scattered light L2, cylindrical lenses 43, 44 without having a power to a component of the scattered light L2 in the vertical direction and having a positive power only with respect to a component of the scattered light L2 in the Y axial direction, a cylindrical lens 45 without having a power with respect to the Y axial direction component and having a positive power with respect to the vertical direction component, a field stop 46 for narrowing down the divergence of the scattered light L2 to a size of the inclined plane of the light intensity detecting device 50, and an ND filter 47, as clearly shown in FIG. 2.

By a difference of magnification between the power in the Y axial direction and the power in the vertical direction with the above mentioned three cylindrical lens 42, 43, and 44, the imaging magnification in the Y axial direction is about 70 times, and the imaging magnification in the vertical direction is about equal (one time). For example, when the major axis along the Y axial direction of the irradiation area 220 is 0.14 mm, a length of opening along the Y axial direction of the field stop 46 is set to 9.8 mm (=0.14×70).

A position in which the field stop 46 is disposed is conjugate with the Y axial direction and the vertical direction of the scattered light detecting optical system 40.

In this embodiment, a focal length and an aperture number of the condenser lens 41 are set to f=21 mm and NA=0.3, respectively, a focal length of the cylindrical lens 43 is set to f=210 mm, and focal lengths of the both cylindrical lenses 44, 45 are respectively set to f=21 mm.

In each of the drawings, a light track, a curvature of lens, a distance between lenses, and the like are schematically shown, so that the focal length f of each of the above-mentioned lenses 41, 43 to 45 is not specifically shown.

The cylindrical lenses 43, 44 structures so called a telecentric optical system, and an image of the scattered light emitted from the irradiation area 220 is focused onto a position P.

On the other hand, the light intensity detecting device 50 decomposes the entered scattered light L2 into the 10 channels (ch) arranged along the Y axial direction. The light intensity detecting device 50 comprises a multi-anode PMT 51 for detecting light intensity of each of the decomposed channels ch1 to ch10, ten amplifiers 52 (from an amplifier 52a corresponding to the ch1, an amplifier 52b corresponding to the ch2, . . . , an amplifier 52j corresponding to the ch10) for respectively amplifying an signal indicating light intensity output from each of the channels ch1 to ch10, ten BPFs 53 (band pass filters) for respectively eliminating a predetermined noise component from the signal amplified by each amplifier, and ten A/D converters 54 for respectively converting the signal passing each BPF into a digital signal, ten memories 55 for respectively storing the digital signal digitized by each A/D converter 54, and an analysis device 56 for determining a size, type, and the like of a defect on the inspected surface 210 in the irradiation area 220 based on the digital signal according to the light intensity for each channel stored in each memory 55.

Figure 3:
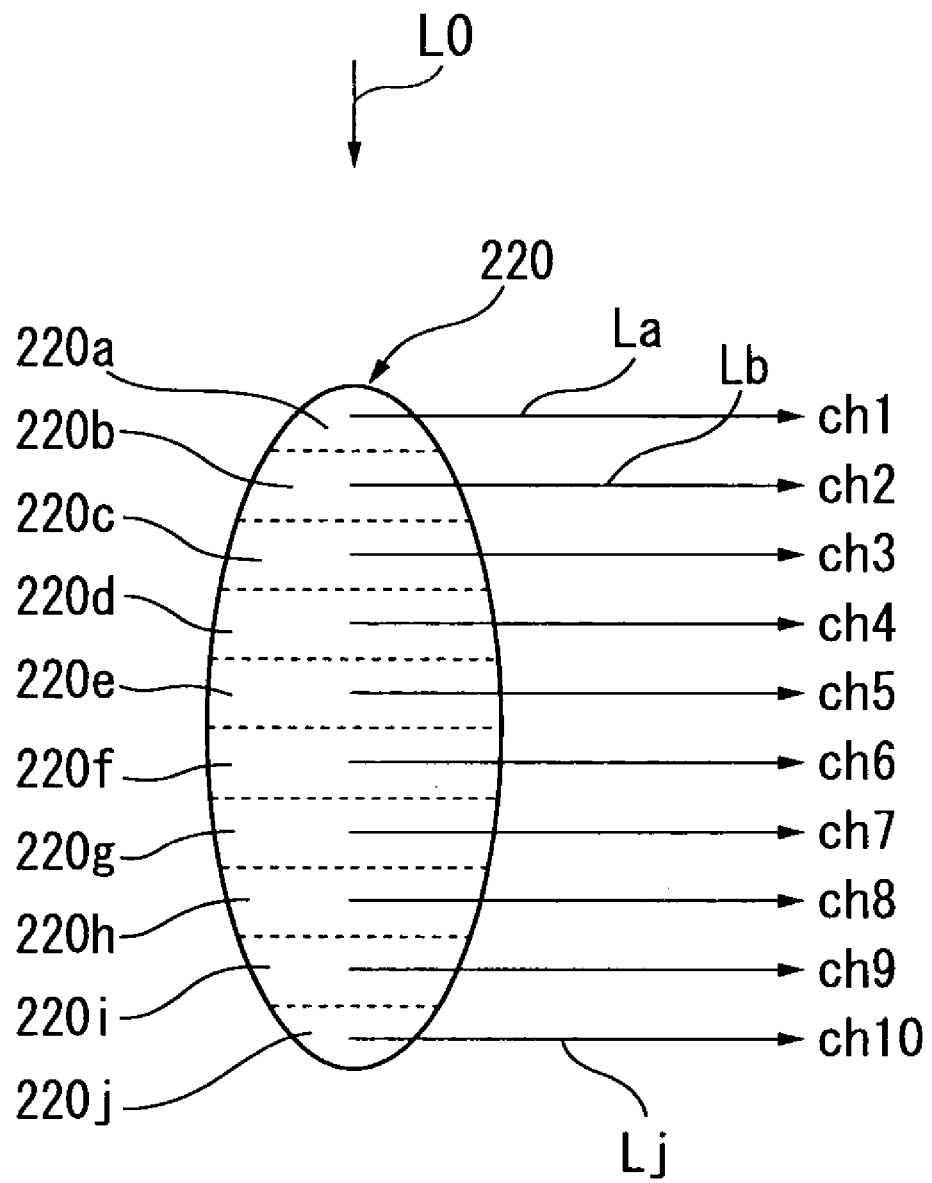
FIG. 3 is a view illustrating a relationship between decomposed regions of an irradiation area and channels decomposed by a multi-anode PMT.

Here, the ten channels ch1 to ch10 of the multi-anode PMT 51 correspond to ten regions 220a to 220j divided along the Y axis direction of the irradiation area 220 as illustrated in FIG. 3 by the relationship with the scattered light detecting optical system 40. The scattered light La (shown by solid line) emitted from the first regions 220a is entered to the ch1, the scattered light Lb emitted from the second region 220b is entered to the ch2, and the scattered light Lj (shown by dotted line) emitted from the tenth region 220j is entered to the ch10.

In addition, instead of including the analysis device 56, the light intensity detecting device 50 may be configured to have a displaying device for displaying the digital signal according to the light intensity for each channel stored in each memory 55 as a graph or a digital signal for each channel, for example. The light intensity detecting device 50 may also be constituted to include a printer or a plotter which prints the digital signal according to the light intensity for each channel as a graph or prints as a digital numerical value.

Gains of the ten amplifiers 52a, 52b, . . . , 52j provided corresponding to the channels ch1, . . . , are not the same with respect to each other, and are set to be different values from each other so as to standardize output values from the channels ch1, . . . , ch10, so that the light intensity distribution of the laser beam L0 with respect to the regions 220a, 22b, . . . , 220j in the irradiation area 220 is deemed to be uniform virtually.

In other words, the laser beam L0 entered in the inspected surface 210 has no uniform light intensity distribution in transverse section, but has Gaussian distribution.

Figure 5A:
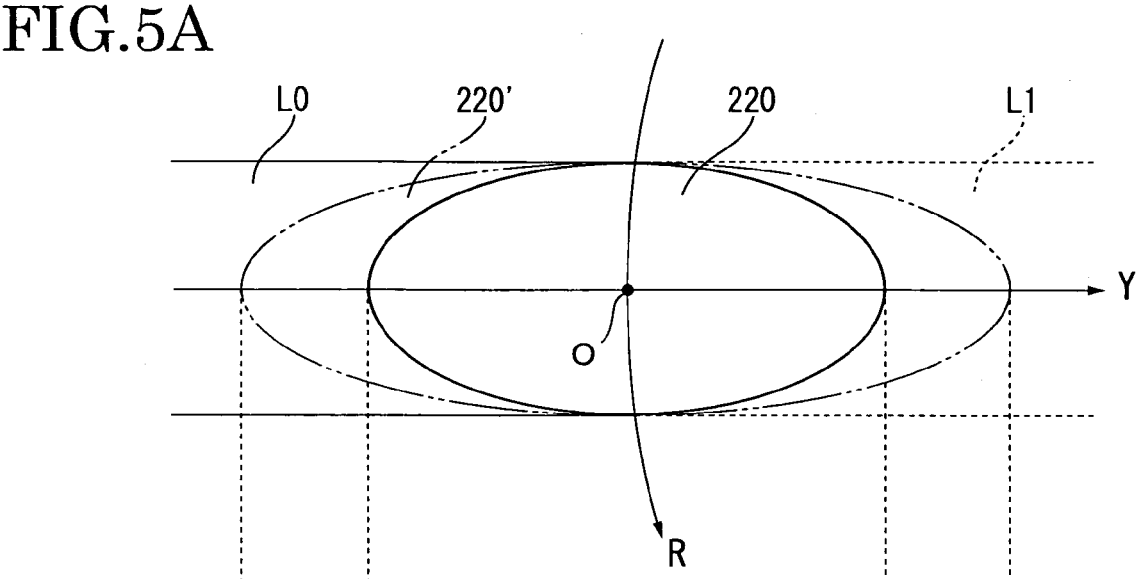
FIG. 5A is a schematic view illustrating a relationship the irradiation area and a real irradiation area.
Figure 5B:
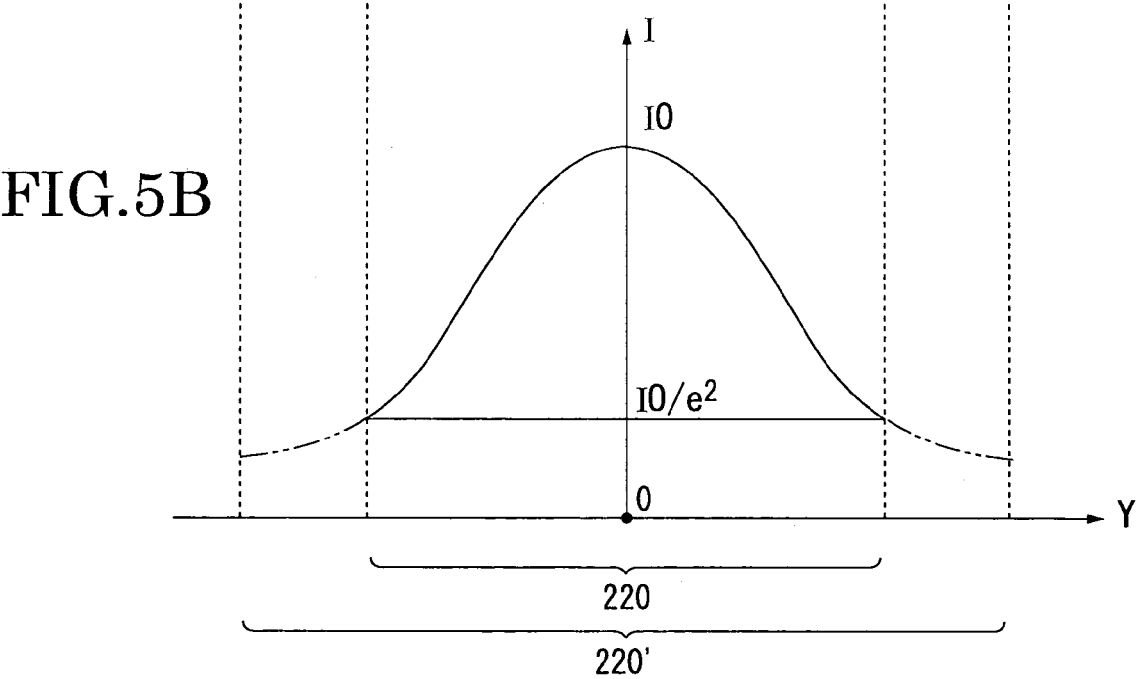
FIG. 5B is a view illustrating intensity distribution of received light in the irradiation area in FIG. 5A along a Y axis.
Figure 6:
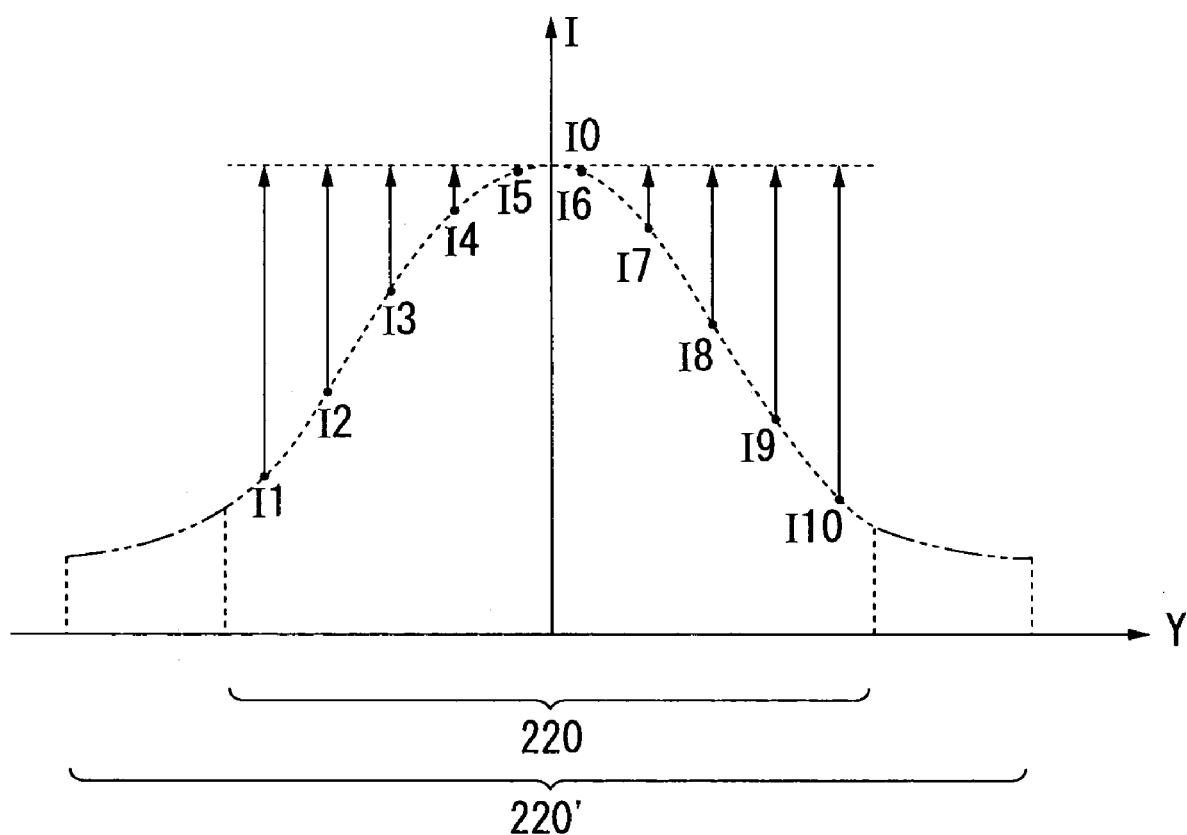
FIG. 6 is a view illustrating a concept of standardization or compensation processing when intensity distribution of received light is deemed to be uniform.

In the irradiation area 220 in which the laser beam L0 having the light intensity distribution as described above is entered, intensity I of light received on the irradiation area, every each position in the Y axial direction has generally Gaussian distribution which is large in the center O of the irradiation area 220 and becomes less as nearing to a peripheral edge of the irradiation area, depending on the light intensity distribution of the laser beam L0, as shown in FIG. 5 B.

If the intensity of the received light in the irradiation area 220 has un-uniform distribution among the regions 220a, 220b, . . . ,220j (see FIG. 3) along the Y axis, even if the same defect is existed in the regions 220a, 220b, . . . , 220j, the intensity of the decomposed scattered light detected in each of the regions 220a, 220b, . . . , 220j has a distribution depending on the distribution of the intensity I of the received light.

Therefore, the gain of each of the amplifiers 52a, 52b, . . . , 52j may be set by entering previously the laser beam L0 into a reference inspected surface under the same conditions as in the surface inspection, obtaining the intensity of the received light in each of the regions 220a, . . . , 220j to correspond to the intensity of each decomposed scattered light from the regions 220a, 220b, . . . , 220j of an irradiation area 220 formed on the reference inspected surface, and correcting the intensity I1, I2, . . . , or I10 of each received light to an uniform intensity I0, I0, . . . , I0.

Consequently, the gains of the amplifiers 52e and 52f connected to the channels ch 5 and ch 6 corresponding to the regions (for example, the regions 220e and 220f and so on) in the vicinity of the center O in the Y axial direction of the irradiation area 220 are set to be most less, and a gain of the amplifier 52 connected to the ch corresponding to the region far away from the center O in the Y axial direction of the irradiation area 220 is more large. The gains of the amplifiers 52a and 52j connected to the channels ch1 and ch10 corresponding to the most far away regions from the center O in the Y axial direction of the irradiation area 220, for example, the regions 220a and 220j and so on, in FIG. 3, are set to be most large.

Because the cylindrical lenses 43, 44 structures the telecentric optical system, principle ray of each scattered lights La to L j, which is emitted from each region 220a to 220j and passed the cylindrical lens 43 is parallel to the optical axis O2.

Moreover, in the surface inspection device 100 comprising the light intensity detecting device 50 having a display device, a printer, and the like, instead of the analysis device 56, a determination such as a defect size and a defect type of the inspected surface 210 in the irradiation area 220 can be made by an analyst observing output information which is based on information displayed on the display device or information printed on a media such as a paper.

Of course, the analysis device 56 may be configured to include the above described display device and the printer.

Next, an operation of the surface inspection device 100 according to the present invention will be explained.

The laser beam L0 is first emitted from the LD10, and the emitted laser beam L0 is projected in the vicinity of the center O on the Y axis in the inspected surface 210 of the wafer 200 at the depression angle α from the negative direction of the Y axis, by the irradiation optical system 20.

At this time, the oval irradiation area 220 having the major axis in the Y axial direction is formed on the portion of the inspected surface 210, in which the laser light L0 is entered. When the defects such as the scratch and the attachment of the foreign matter are not existed on the irradiation area 220, the remaining light L1 except for light which is absorbed by the irradiation area 220 is emitted in the Y axial positive direction at the reflection angle (90°−α) of the same angle with the incident angle (90°−α) as the regular reflection light.

Therefore, the light is not essentially emitted to the direction to which the regular reflection light L1 is emitted.

On the contrary, when the scratch is existed on the irradiation area 220, the laser beam L0 is reflected diffusely by a microscopic asperity and the like forming the scratch, so that the scattered light is generated by the diffuse reflection other than the regular reflection light L1.

Similarly, when the foreign matter is adhered or attached to the irradiation surface 220, the laser beam L0 is reflected diffusely by a convex wall of the foreign matter and so on, so that the scattered light is caused by the diffuse reflection other than the regular reflection light L1.

At this time, the intensity I of the scattered light emitted from the regions 220*a*, . . . , of the irradiation area 220 depends on the light intensity distribution of the laser beam L0.

Accordingly, one portion L2 of the scattered light (hereinafter referred to as scattered light) generated by the existence of the defect such as the scratch and the foreign matter is substantially perpendicular to the Y axis, and is entered to the scattered light detecting optical system 40 having the optical axis O2 directed to the irradiation area 220 at a depression angle β with respect to the inspected surface 210.

On the contrary, when the laser beam L0 is emitted from the LD10, the turning stage 31 comprising the scanning device 30 is turned in the direction arrow R at a constant angular velocity, and the turning stage 31 is moved in the arrow direction (Y axial positive direction) at a constant velocity by the liner motor 32.

Therefore, the irradiation area 220 on the inspected surface 210 of the wafer 200 provided on the turning stage 31 relatively moves in the spiral shape on the inspected surface 210, as shown in FIG. 2A. As a result, the laser beam L0 scans the inspected surface 210 in the spiral state.

A width of pitch of the scanning locus in the radial direction of the wafer 200 can be adjusted through adjustment of at least one of the turning angular velocity of the turning stage 31 or the displacement velocity of the liner motor 32. The laser beam L0 is capable of scanning the entire inspected surface 210 by adjusting the pitch of the scanning locus, while adjusting the size of the irradiation area 220.

When the defect is existed on the irradiation area 220 and the scattered light L2 generated by the defect is condensed by means of the condenser lens 41 of the scattered light detecting optical system 40, and the wave surface of the scattered light L2 is adjusted by means of the polarizing plate 42. After that, the scattered light L2 is entered into the cylindrical lenses 43, 44, 45, and incident of light (including backlight) except from the irradiation area 220 is eliminated by the filed stop 46, and is reduced by the ND filter 47, and then is entered into the multi-anode PMT51.

Meanwhile, in this embodiment, in order to simplify the explanation, the entire irradiation area 220 where the laser beam L0 is entered onto or into the inspected surface is adopted as a detecting object of the scattered light. However, correctly, a region at 220' shown in chain double-dashed line in FIG. 5A is a real irradiation area, which is the area in which the laser beam L0 is entered and the region referred to as the irradiation area 220 shown in solid line is a region having light intensity I more than a predetermined proportion $I0/e^2$ to the most light intensity I0, the real irradiation area 220' and is an area which is detected object of the scattered light L2.

The irradiation area 220 is formed by stopping down the scattered light L2 from the real irradiation area 220' by use of the field stop 46, but it is explained in the specification except for a case particularly referred, as already described that the irradiation area 220 is the same with the real irradiation area 220'.

Since the inclined plane of the scattered light L2 is divided into the ten regions for detecting light intensity such as ch1 to ch10 in the Y axial direction, i.e. major axis direction of the irradiation area 220, the multi-anode PMT51 spatially decomposes the scattered light L2 emitted from the irradiation area 220 in the major axis direction or Y axial direction.

Accordingly, as illustrated in FIG. 3, the ch1 of the multi-anode PMT 51 detects the light intensity of the scattered light La emitted from the region 220*a*, which is positioned in the vicinity of the longest diameter of the Y axial negative direction in the major axial direction of the irradiation area 220, from the scattered light L2 emitted from the irradiation area 220. The ch2, correspondingly, detects the light intensity of the scattered light Lb emitted from the area 220*b* adjacent to the area 220*a* from the scattered light L2 emitted from the irradiation area 220, and the ch10 detects the light intensity of the scattered light Lj emitted from the area 220*j*, which is positioned in the vicinity of the longest diameter of the Y axial positive direction, from the scattered light L2 emitted from the irradiation area 220.

The light intensity of each of scattered lights La to L j detected every the regions 220*a* to 220*j* of the irradiation area 220, by the channels ch 1 to ch 10 of the multi-anode PMT 51 is photo-electrically converted and is outputted as a predetermined electrical signal.

In addition, at this step, the light intensity of each scattered light depends on the intensity distribution of the laser beam L0 as described above.

Those output signals are respectively input to each amplifier 52, and then the signals are amplified by the each amplifier 52 provided corresponding to the each channel of ch1 to ch10.

Because the gains of the amplifiers 52*a*, 52*b*, . . . , 52*j* are set to be different values in such a manner that the light intensity signal values of the scattered lights La to L j are standardized to signal values which will be obtained if the intensity distribution of the laser beam L0 is uniform, as described above, the light intensity signal values of the scattered lights La to L j are standardized.

As a result, the light intensity signal values outputted from the amplifiers 52a, 52b, . . . , 52j are not depended on the intensity distribution of the laser beam L0 and have a high accuracy.

In addition, the standardized light intensity signals are inputted into corresponding BPF 53, respectively, and a component of a predetermined noise is removed, and then are inputted into an A/D converter 54 to be digitalized and the digitalized signals are stored into a corresponding memory 55.

In this way, when the digital signal for displaying each intensity V of the scattered light of La to Lj stored in each memory 55 is analyzed by the analysis device 56. With this analysis device 56, if the scratch formed through a number of areas on the irradiation area 220 is existed as shown in FIG. 4A, each intensity V of the scattered light La to Lj respectively read from the memory 55 corresponding to each channel is recognized as a positive output V continued between a number of channels as illustrated in FIG. 4D.

On the contrary, as shown in FIG. 4C, if the foreign matters are dotted with some regions in the irradiation area 220, the intensity V of the scattered light La to Lj respectively read from the memory 55 corresponding to each channel is recognized as positive outputs V in a plurality of channels, but the channels including the positive outputs are not continued, and they are separated, as shown in FIG. 4F.

Accordingly, when the light intensity V of a predetermined level or higher is detected by a channel, and the light intensity of the substantially same level is detected in the channels adjacent to this channel, and then a number of channels by which such light intensity V is detected is continued (FIG. 4D), the light intensity V can be analyzed and determined that a large defect (such as a scratch) extending in the Y axial direction in the irradiation area 220 corresponding to the arrangement direction (Y axial direction) of the channel is presented.

On the other hand, although the light intensity V of a predetermined level or higher is detected by a channel, if the light intensity V detected in the channels adjacent to the channel is light intensity V indicating a significant difference from a predetermined level (FIG. 4F), or although the light intensity V of the substantially same level is detected in adjacent channels, if the channels detected such light intensity V are continued only for 2 or 3 channels (FIG. 4E), the defect is not a defect continued in a predetermined direction within the irradiation area, and the defect is analyzed and determined as a small defect (such as adhesion of a foreign matter) illustrated in FIG. 4C and FIG. 4B.

As a result, a plurality of small defects and a single large defect, which are difficult to be identified, can be easily identified.

Moreover, the existence position of the defect in the irradiation area 220 can be preciously detected at least in the arrangement direction of the channel.

Further, when the defect is distinguished between the formed scratch and the adhered foreign matter, the scratch is formed into relatively longer state than the foreign matter, and the foreign matter has a small size in many cases, so that the scratch and the foreign matter can also be distinguished accurately depending upon the length, or long and short of the size.

Accordingly, as shown in FIG. 4D, when the light intensity V is detected continuous to a number of channels, the light intensity V can be determined as a long size defect, i.e. a scratch. At the same time, as shown in FIGS. 4E and 4F, when the light intensity V is detected continuous to the adjacent two or three channels, or when the light intensity V is detected in a single channel, the light intensity V can be determined as a short size defect, i.e. a foreign matter.

Although the embodiment explains that the scattered light L2 is emitted from the irradiation area 220, actually, the scattered light L2 also can be emitted from the real irradiation area 220'.

Here, If the irradiation area 220 is a region of the detected object of the scattered light L2, it is required that the pitch P1 of the scanning locus S the laser beam L0 for scanning the inspected surface 210 is set to be less than at least length along the Y axial direction of the irradiation area 220 or a length of a major axis of the irradiation area.

In the conventional surface inspecting apparatus, because the intensity of the received light of the laser beam L0 is too less or $I0/e^2$ less relative to that of the other area with respect to an area of the real irradiation area 220' outside than the irradiation area 220, the irradiation area must be set to the area of the detected object of the scattered light L2.

On the contrary, in the surface inspecting apparatus 100 in the embodiment, because it is possible to be uniform the intensity distribution of the received light of the irradiation area 220, it is possible to be uniform to the same degree as the intensity of the received light of the irradiation area 220, with respect to intensity distribution of received light in the area of the real irradiation area 220' outside than the irradiation area 220.

Therefore, to enlarge the area of the detected object to real irradiation area 220', it is also possible to adopt a structure in which the gain of the amplifier 52 is set adequately by removing the field stop 46 of the scattered light detecting optical system 40 and increasing the number of channels in the multi-anode PMT 51, according to the enlargement of the area of the detected object.

Figure 7:
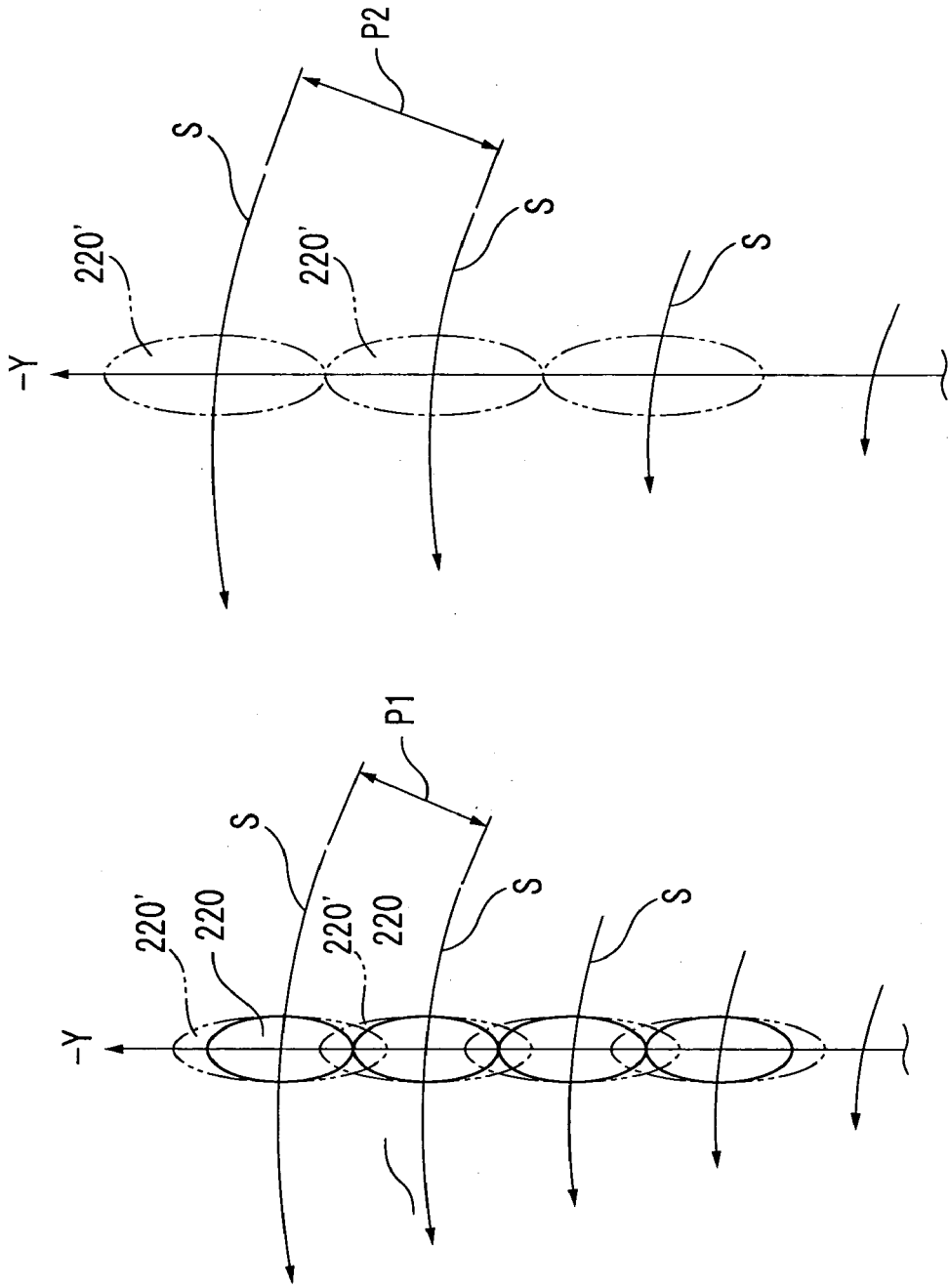

According to the surface inspecting apparatus structured as described above, because the area of the detected object of the scattered light L2 can be enlarged to the real irradiation area 220', it is possible to enlarge the pitch P2 of the scanning locus S of the laser beam L0 for scanning the inspected surface 210 than the pitch P1 at the time the irradiation area 220 is the area of the detected object, as shown in FIG. 7B.

Accordingly, it is possible to increase a speed of scanning in the Y axial direction and to achieve reduction of a time of operation.

Meanwhile, in the surface inspecting apparatus 100 and the surface inspecting method in the embodiment, although the intensity of the decomposed scattered light detected every each channel is standardized by adjusting the gain of the amplifier 52 of the light intensity detecting device 50, the present invention is not limited to the embodiment, the standardization may be achieved by means of process of signal through an imaging processing device such as an analysis means 56 or the other un-illustrated control means.

Second Embodiment

Figure 8:
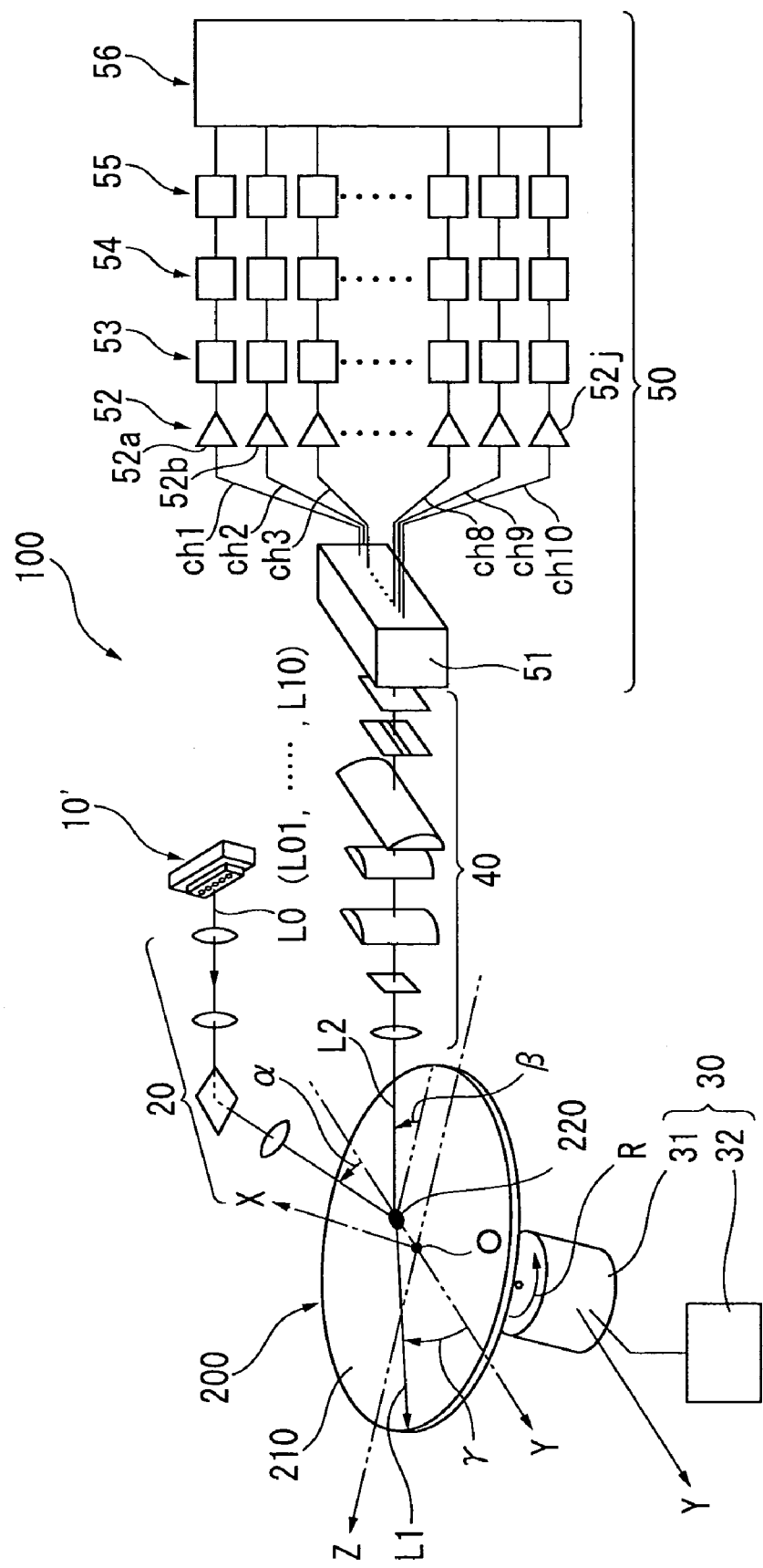
FIG. 8 is a schematic structural view illustrating a surface inspecting apparatus according to a second embodiment of the present invention.

FIG. 8 illustrates a surface inspecting apparatus 100 in a second embodiment of the present invention.

The illustrated surface inspecting apparatus 100 comprises a multi-LD 10' for emitting ten (10) laser beams L0, L01, L02, . . . , L10, an illumination optical system 20 for entering the ten laser beams L0 emitted from the multi-LD 10' into the inspected surface 210 of the wafer 200 which is generally a perfect circular plate, at a predetermined depression angle α, in such a manner that a portion of the laser beams is arranged to superpose in the Y axial direction, a scanning device 30 for displaying the wafer 200 so that the laser beams L0 scan spirally the inspected surface 210, a light intensity detecting device 50 for detecting intensity of the entered light, and a scattered light detecting optical system 40 for guiding scattered lights L2 emitted from the irradiation area 220 (see FIG. 9) which is formed into an elongated shape, by the ten laser beams L01, . . . , being entered into the irradiation area in an arranged state, to the light intensity detecting device 50.

Here, the ten laser beams L01, . . . , emitted from the multi-LD 10' are set to be approximately the same light intensity with respect to each other.

A basic structure and an operation thereof in each of the illumination optical system 20, the scattered light detecting optical system 40 and the light intensity detecting device 50 are the same as in the surface inspecting apparatus 100 in the first embodiment as described above, if there no special mention.

In addition, in the light intensity detecting device 50, the amplifiers 52a, . . . , have no different gains, respectively, and all the amplifiers 52a, . . . , have the same gain.

An operation of the surface inspecting apparatus 100 in the second embodiment will be explained below.

The ten laser beams L0 are first emitted from the multi-LD 10', the emitted ten laser beams L0 are entered into the vicinity of the center O on the Y axis in the inspected surface 210 of the wafer 200 at the depression angle a from a minus direction of the Y axis into the state arranged in the Y axial direction, through the illustration optical system 20.

Figure 9:
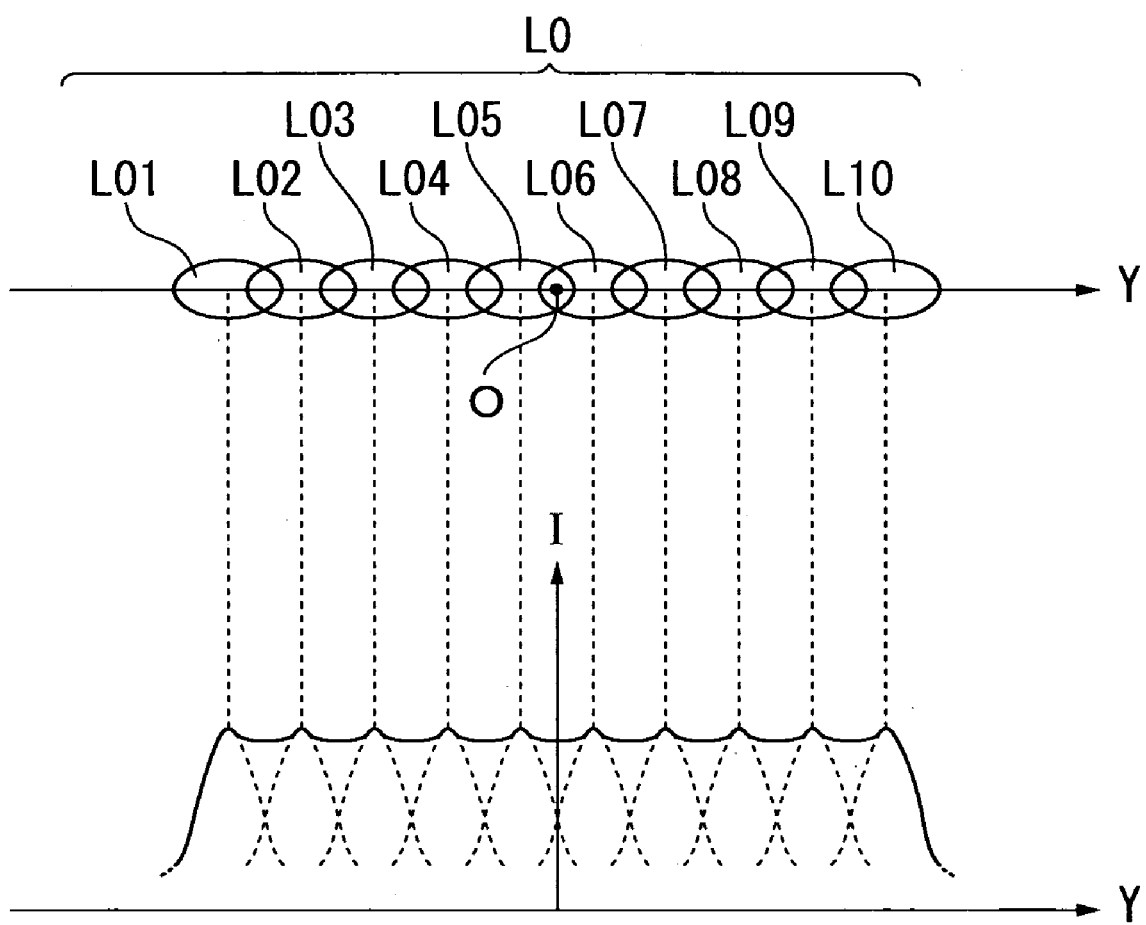
FIG. 9 is a view illustrating irradiation spots by laser beams and intensity distribution of received light, in the surface inspecting apparatus as shown in FIG. 8.

At this time, the elongated irradiation area 220 extending in the Y axial direction is formed on a portion of the inspected surface in which the ten laser beams L0 are entered, as shown in FIG. 9.

Here, although intensity distributions of the laser beams L01, L02, . . . , L10 received on the irradiation area 220 have Gaussian distributions, respectively, because bases of distributions of the adjacent laser beams L01 and L02, L02 and L03, . . . , L09 and L10 are superposed with respect to each other, uniformity of the intensity distribution of the received light on the irradiation area 220 in the Y axial direction is increased comparing with that in the entrance of a single laser beam only, by superposition principle as shown in FIG. 9. The intensity distribution of the received light is set to become uniform in the embodiment.

As a result, an electrical signal showing each intensity of the decomposed scattered lights La to Lj, which are emitted from the irradiation area 220 and are detected photo-electrically by the channels ch 1 to ch 10 of the multi-anode PMT 51 through the scattered light detecting optical system 40 are depended on the generally uniform intensity distribution of the received light and therefore are accurate than as in the prior art, thereby becoming high reliable signal values.

Consequently, it is possible to perform detailed analysis of the defect such as the gravity thereof.

Meanwhile, in the embodiment, although the number of the laser beams L0 entering into the inspected surface of the semi-conductor wafer 200 is ten and is the same as that of the ten decomposed detected channels of the multi-anode PMT 51, it is not necessary to set the two to the same number in the surface inspecting apparatus and the surface inspecting method according to the present invention.

In other words, the number of the decomposed detected channels of the multi-anode PMT 51 may be set more than that of the laser beams L0, whereas the number of the laser beams L0 may be set more than that of the decomposed detected channels of the multi-anode PMT 51.

In addition, in the aforementioned first and second embodiments, the major axial direction of the irradiation area 220 is disposed along a normal direction of spiral of the scanning locus by the linear motor 32 moving the wafer 200 along the Y axial direction at a constant speed, but the surface inspecting apparatus and method in the present invention are limited to the manners of the these embodiments.

In other words, the present invention makes it possible to use a structure in which the irradiation optical system is disposed so as to form the irradiation area 220 on a Z axis of the inspected surface 210 and the linear motor moves the wafer 200 at the constant speed along the Z axis. In this case, the direction of the major axis of the irradiation area 220 is disposed along a direction of tangent of spiral of the scanning locus.

In the first and second embodiments, although the scanning locus formed on the inspected surface 210 of the wafer 200 is a spiral directing from the center O of the wafer 200 to the outer peripheral edge thereof, the scanning locus may be a spiral directing from the outer peripheral edge of the wafer 200 to the center O by setting an initial position of the irradiation area 220 on the inspected surface 210 to the outer peripheral edge of the wafer 200, even though this form is used, it is possible to obtain the same operation and effect as in the embodiments.

Moreover, the scanning locus by the scanning device 30 is not limited to the spiral as the embodiments, for example, may be a plurality of concentric circles. That is to say, it is possible to form a scanning locus, in which after scanning one circle, the next circle is scanned through radial movement of the wafer. In other words, tracks are sequentially scanned.

Of course, the scanning locus may be formed into a mere zigzag state. According to the scanning device 30 capable of forming the smooth spiral scanning locus as in the embodiments, the scanning device is difficult to be placed under influence of an inertial force of the inspection object or wafer 200 and therefore it is possible to increase reliability of the surface inspecting apparatus 100.

According to the embodiments, the scattered light from the elliptic irradiation area 220 is decomposed spatially with respect to the direction of the major axis of the elliptic irradiation area and the light intensity of the decomposed scattered light is detected.

However, in the surface inspecting apparatus and method according to the present invention, the scattered light may be decomposed spatially with respect to a direction of a minor axis of the ellipse of the irradiation area and intensity of the decomposed scattered light may be detected. Moreover, the irradiation area is not elliptic and may be formed into a perfect circle. In this case, it is better to set refractive powers with respect to directions perpendicular and parallel to the inspected surface by the illumination optical system, in accordance with the incident or depression angle of each laser beam into the inspected surface.

Although the preferred embodiments have been described, the present invention is not limited to the embodiments, various modifications and changes can be made to the aforementioned embodiments.

What is claimed is:

1. A method for inspecting a surface, comprising:
  entering a predetermined luminous flux at a predetermined incident angle in an inspected surface of an inspection object which is an object of a surface inspection;

displaying relatively at least one of the luminous flux and the inspection object so that the luminous flux scans upon the inspected surface;

decomposing spatially light intensity of scattered light reflected on an area of the inspected surface entering the luminous flux into a plurality of channels with respect to an one-dimensional direction corresponding to a predetermined direction in the area of the inspected surface entering the light flux;

performing inspection of the inspected surface by detecting individually light intensity of each of the decomposed scattered lights obtained by the decomposition; and increasing uniformity of light intensity distribution with respect to at least the predetermined direction in the area of the inspected surface in which the luminous flux is entered.

2. The method for inspecting a surface according to claim 1, comprising setting uniformly the light intensity distribution of light by entering the plurality of luminous flux into the area of the inspected surface so that the plurality of luminous flux are arranged in the predetermined direction.

3. A method for inspecting a surface, comprising:
entering a predetermined luminous flux at a predetermined incident angle in an inspected surface of an inspection object which is an object of a surface inspection;

displaying relatively at least one of the luminous flux and the inspection object so that the luminous flux scans upon the inspected surface;

decomposing spatially light intensity of scattered light reflected on an area of the inspected surface entering the luminous flux into a plurality of channels in an one-dimensional direction corresponding to a predetermined direction in the area of the inspected surface entering the luminous flux;

performing inspection of the inspected surface by detecting individually light intensity of each of the decomposed scattered lights obtained by the decomposition; and standardizing light intensity distribution of the detected decomposed scattered lights in the one-dimensional direction, according to the light intensity distribution with respect to at least the predetermined direction in the area of the inspected surface in which the luminous flux is entered.

4. The method for inspecting a surface according to claim 1 or 3, wherein the predetermined direction is substantially perpendicular to a direction in which the luminous flux scans the inspected surface.

5. An apparatus for inspecting a surface, comprising:
a light source for emitting a predetermined luminous flux;
an irradiating optical system for entering at a predetermined incident angle the luminous flux emitted from said light source into an inspected surface of an inspection object which is an object of a surface inspection;
a scanning device to relatively displace at least one of said luminous flux and said inspection object so that said luminous flux scans on said inspected surface;
a light intensity detecting device to detect intensity of the entered light; and
a scattered light detecting optical system for guiding scattered light emitted from an area of said inspected surface in which said luminous flux is entered into the light intensity detecting device,
said light intensity detecting device being set to decompose said scattered light into a plurality of channels at least in a one-dimensional direction in an inclined plane of the light intensity detecting device and to detect the light intensity, in order to increase uniformity of light intensity distribution with respect to at least the predetermined direction in the area of the inspected surface in which the luminous flux is entered.

6. The apparatus for inspecting a surface according to claim 5, wherein said light source emits a plurality of luminous fluxes, said irradiating optical system setting substantially uniformly the light intensity distribution with respect to the predetermined direction by entering the plurality of luminous fluxes in the area of the inspected surface in such a manner that the plurality of luminous fluxes emitted from the light source are arranged in the predetermined direction.

7. An apparatus for inspecting a surface, comprising:
a light source for emitting a predetermined luminous flux;
an irradiating optical system for entering at a predetermined incident angle the luminous flux emitted from said light source into an inspected surface of an inspection object which is an object of a surface inspection;
a scanning device to relatively displace at least one of said luminous flux and said inspection object so that said luminous flux scans on said inspected surface;
a light intensity detecting device to detect intensity of the entered light; and
a scattered light detecting optical system for guiding scattered light emitted from an area of said inspected surface in which said luminous flux is entered into the light intensity detecting device,
said light intensity detecting device being set to decompose said scattered light into a plurality of channels at least with respect to a one-dimensional direction in an inclined plane of the light intensity detecting device and to detect the light intensity, in order to standardize light intensity distribution of the detected decomposed scattered lights in the one-dimensional direction, according to the light intensity distribution with respect to at least the predetermined direction in the area of the inspected surface in which the luminous flux is entered.

8. The apparatus for inspecting a surface according to claim 7, wherein the light intensity detecting device includes an amplifier provided in each channel, a gain of the amplifier corresponding to each channel being set to standardize light intensity distribution of the detected decomposed scattered lights in the one-dimensional direction, according to the light intensity distribution with respect to at least the predetermined direction in the area of the inspected surface in which the luminous flux is entered.

9. The apparatus for inspecting a surface according to claim 5, wherein the predetermined direction is set to be substantially perpendicular to a direction in which the luminous flux scans the inspected surface.

* * * * *